United States Patent
Dutta et al.

(10) Patent No.: US 11,596,555 B2
(45) Date of Patent: Mar. 7, 2023

(54) WOUND DRESSING FOR COMBINED NEGATIVE PRESSURE AND FLUID DELIVERY SYSTEM

(71) Applicant: SECRETARY, DEPARTMENT OF BIOTECHNOLOGY, New Delhi (IN)

(72) Inventors: Neelarnab Dutta, Jorhat (IN); Roshan Gurung, Brisbane (AU); Shivani Gupta, Bathinda (IN); Taihei Fujii, Yonago (JP); Sushma Sagar, New Delhi (IN)

(73) Assignee: SECRETARY, DEPARTMENT OF BIOTECHNOLOGY, New Delhi (IN)

( * ) Notice: Subject to any disclaimer, the term of this patent is extended or adjusted under 35 U.S.C. 154(b) by 392 days.

(21) Appl. No.: 16/492,465

(22) PCT Filed: Mar. 8, 2018

(86) PCT No.: PCT/IB2018/051505
§ 371 (c)(1),
(2) Date: Sep. 9, 2019

(87) PCT Pub. No.: WO2018/163093
PCT Pub. Date: Sep. 13, 2018

(65) Prior Publication Data
US 2021/0137746 A1   May 13, 2021

(30) Foreign Application Priority Data
Mar. 9, 2017 (IN) .............................. 201711008310

(51) Int. Cl.
*A61F 13/02* (2006.01)
*A61M 1/00* (2006.01)
*A61F 13/00* (2006.01)

(52) U.S. Cl.
CPC ........... *A61F 13/0216* (2013.01); *A61M 1/90* (2021.05); *A61F 2013/00255* (2013.01)

(58) Field of Classification Search
CPC ........ A61F 13/0216; A61F 2013/00255; A61F 2013/0017; A61F 13/00068; A61M 1/90; A61M 1/915
See application file for complete search history.

(56) References Cited

U.S. PATENT DOCUMENTS 5,342,434 A * 8/1994 Wu ...................... A41D 31/102
                                                                96/13
7,534,240 B1   5/2009 Johnson
(Continued)

FOREIGN PATENT DOCUMENTS

WO   2014140578   9/2014

OTHER PUBLICATIONS

"Reticulated Foam: The Properties, Benefits and Applications" Amcon American Converters inc., Nov. 9, 2020, https://amconfoam.com/reticulated-foam-the-properties-benefits-and-applications/# (Year: 2020).*

(Continued)

*Primary Examiner* — Susan S Su
*Assistant Examiner* — Eric Rassavong
(74) *Attorney, Agent, or Firm* — Cantor Colburn LLP

(57) ABSTRACT

A multi-action wound dressing for accelerated wound healing by means of multi-therapeutic action is disclosed. The dressing comprises a porous sheet (101); two flexible sheets (102) having a first sheet (103) and a second sheet (104) attached to each other; multichannel conduits (105) or a plurality of single channel conduits; multichannel tubes (106), side adhesive tapes (107) and an optional wound contact layer (108). The porous sheet (101) includes a top planar surface (201), thickness (202) and a bottom uneven (Continued)

Figure 1A:
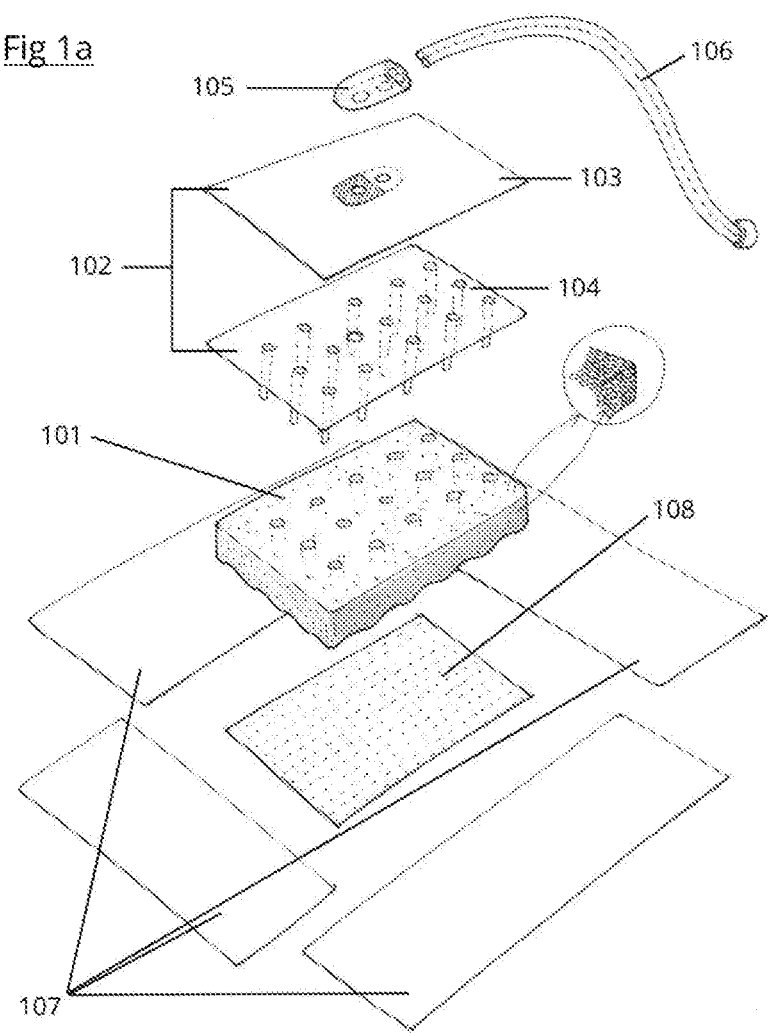

surface (203). The bottom uneven surface (203) lies on the surface of the wound and may have surface patterns (204). The pattern (204) may be wavy patterns and/or any other regular and/or irregular surface protrusion that allow intermediate gaps between wound surface and the bottom surface (203) of the porous sheet through which fluid can flow over the wound surface.

17 Claims, 10 Drawing Sheets

(56) References Cited

U.S. PATENT DOCUMENTS

| | | |
|---|---|---|
| 8,088,113 B2 | 6/2012 | Scherson et al. |
| 9,050,210 B2 | 6/2015 | Olson |
| 9,114,237 B2 | 8/2015 | Randolph et al. |
| 2007/0038172 A1* | 2/2007 | Zamierowski ........ A61M 27/00 604/20 |
| 2010/0106117 A1 | 4/2010 | Lockwood et al. |
| 2010/0121287 A1 | 5/2010 | Smith et al. |
| 2011/0028918 A1* | 2/2011 | Hartwell ........... A61F 13/00068 604/319 |
| 2011/0230848 A1* | 9/2011 | Manwaring ............. A61M 1/90 604/290 |
| 2012/0143114 A1* | 6/2012 | Locke ..................... A61L 15/16 602/43 |
| 2013/0204210 A1 | 8/2013 | Pratt et al. |
| 2015/0032035 A1* | 1/2015 | Banwell ............ A61F 13/00068 601/6 |
| 2015/0164697 A1* | 6/2015 | Malmsjo ................. A61M 1/90 604/543 |
| 2015/0265754 A1* | 9/2015 | Blott ..................... A61M 35/00 604/290 |
| 2015/0320917 A1 | 11/2015 | Randolph et al. |
| 2016/0120706 A1* | 5/2016 | Collinson ........... A61F 13/0253 604/319 |
| 2016/0166781 A1 | 6/2016 | Sarangapani et al. |
| 2018/0110657 A1* | 4/2018 | Locke ..................... A61B 46/40 |

OTHER PUBLICATIONS

International Search Report & Written Opinion; International Publication No. PCT/IB2018/051505; International Filing Date Mar. 8, 2018; dated May 28, 2018; 9 pages.

* cited by examiner

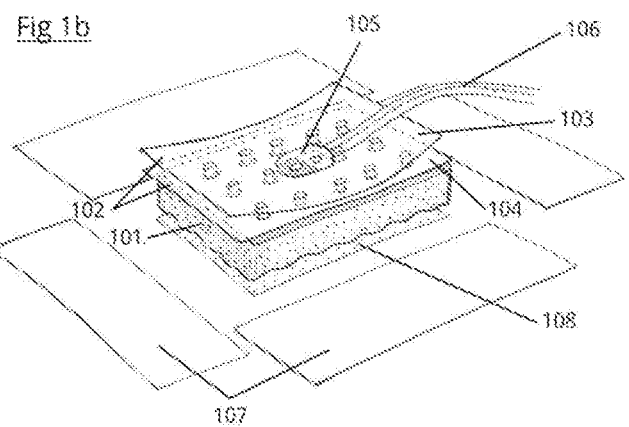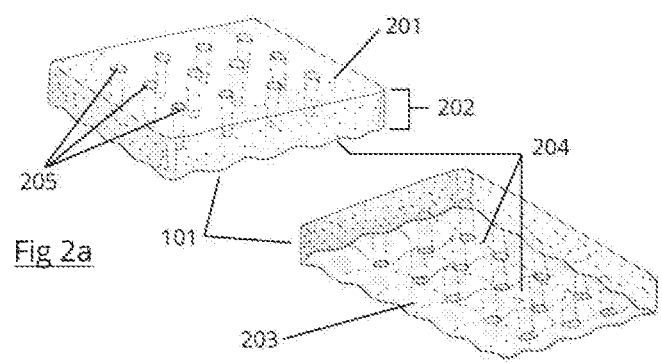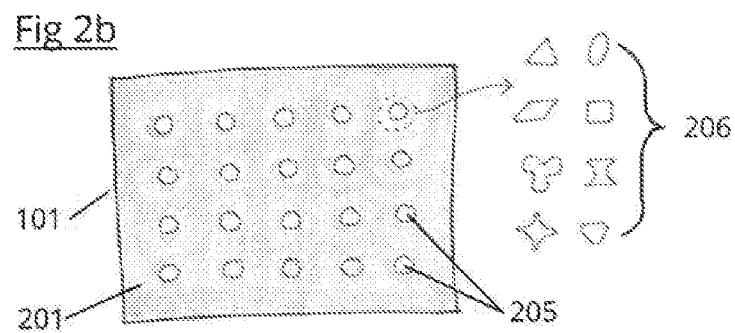

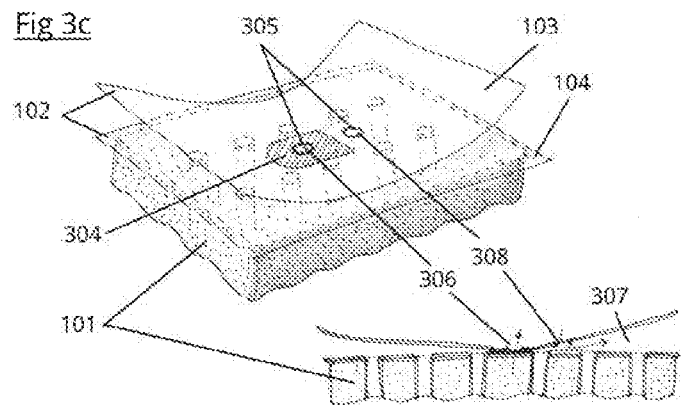
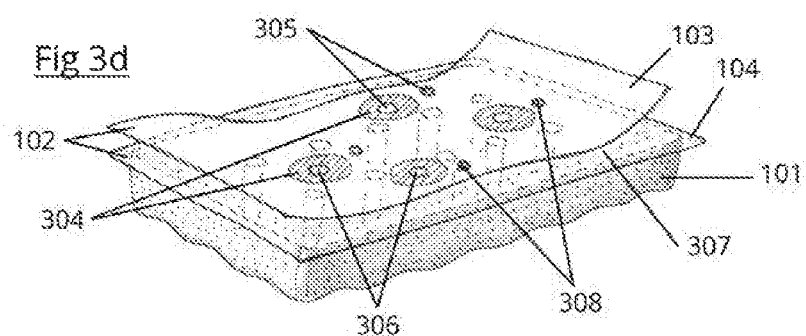
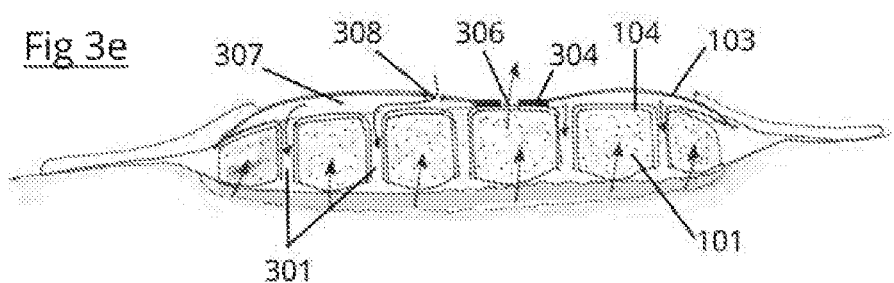

WOUND DRESSING FOR COMBINED NEGATIVE PRESSURE AND FLUID DELIVERY SYSTEM

CROSS REFERENCE TO RELATED APPLICATIONS

This application is a National Stage application of PCT/IB2018/051505 filed on Mar. 8, 2018, which claims the benefit of Indian Application No. 201711008310 filed on Mar. 9, 2017, both of which are incorporated by reference in their entirety herein.

TECHNICAL FIELD OF THE INVENTION

The present subject matter described herein, in general, relates to healing of wounds and wound-treatment therapies, and more particularly, to a dressing for wound healing configured for equal distribution of negative pressure and fluid delivery at wound site to enhance wider range of biomechanism favourable for wound healing.

BACKGROUND OF THE INVENTION

Wound healing is a natural biological process which occurs in four phases starting with haemostasis followed by inflammatory phase and proliferative phase. It then finishes with remodelling phase. Common chronic types of wounds are venous leg ulcers, ischemic wounds, diabetic foot ulcers, and pressure wounds and acute wounds are traumatic wounds, post-surgical wounds and burns.

A wound is classified as a non-healing wound if it does not heal in an orderly and timely manner. These wounds usually do not close without interventions, and are sometimes resistant to healing interventions. Many local and systemic factors may interfere in one or more of phases of healing process and make wounds difficult to heal. Some common features shared by each of these wounds include prolonged inflammation, excessive discharge, persistent infections, and formation of drug-resistant microbial bio films. These non-healing wounds can be exhausting for the affected individual and place a massive financial burden on healthcare systems.

Wounds affect approximately 1% of the population worldwide. In the United States, chronic wounds affect around 6.5 million patients. A conservative estimate of the staggering cost of caring for these wounds exceeds $50 billion per year. The prevalence of chronic wounds in India is reported to be 4.5/1000 population and acute wounds to be 10.5/1000 population. Complications to non-healing wounds are vast including poor quality of life, severe pain, septicaemia, prolonged hospitalization, and in most cases amputations.

The care of these wounds has become its own specialty, with providers often using advanced therapies, including but not limited to growth factors, extracellular matrices, bioengineered skin, oxygen therapy, and negative pressure wound therapy (NPWT). Negative pressure wound therapy has been found useful in treating exudating wounds. But there are limitations of this technology which restricts its use in various clinical conditions. It requires frequent change of dressing in case of contaminated wounds because negative pressure wound therapy does not control microbial growth per se. However, few literature and prior art propose use of NPWT systems with Fluid therapies like use of Antibiotics, Saline water, Oxygenation to take care of microbial growth at the wound site.

For various kinds of wound care systems reference is made to US20130204210, US20100121287, US20150320917 and US20160166781, which discloses few embodiments on the combinations of negative pressure fluid therapy and fluid delivery. However, there are gaps at various aspects of the functional architecture and design such as poor uniform distribution of negative pressure and poor uniform fluid delivery, not being a solo integrated wound care device, lack of smart control logic to use combination of therapies in an optimized way.

The dual action wound healing device is described in U.S. Pat. No. 8,088,113B2 where a portable, self-contained device is used for the topical application of oxygen and the removal of wound exudates to promote the healing of skin wounds. However, the working principle of the device cannot provide oxygen and negative pressure simultaneously. Also, there is no provision for the user to set specific negative pressure and duty cycle.

Reference is also made to US 20100106117 A1 which describes about a wound treatment apparatus which comprises of a vacuum therapy along with a wound dressing member that only allows for irrigation. The wound dressing member claims that the presence of open spaces in the design allows for a generally uniformly distributed vacuum therapy to draw exudates from the wound. However, the system works only with liquid mainly for the purpose of irrigation. It is unable to deliver other fluids such as oxygen. The application procedure for the bandage also requires multiple steps Reference is made to U.S. Pat. No. 9,050,210, which describes a system for applying reduced pressure along with a porous pad along with a drape positionable over the porous pad to seal. The system focuses on the intricacies of the porous pad and the possible arrangement of it. However, the system is not suited for delivery of any fluids including oxygen. As such, the system is unable to carry out dual therapy with negative pressure and fluid delivery.

Reference is also made to U.S. Pat. No. 9,114,237, which provides systems and methods for delivery of fluid to wound therapy dressing wherein, a pressure source provides negative pressure to a wound dressing and a positive pressure to an actuator that expels fluid from a fluid reservoir.

Further, Reference is also made to U.S. Pat. No. 7,534,240 B1, which relates to a method and apparatus for the introduction to a wound under negative pressure therapy for a wound healing agent, which generally comprises a foam pad for insertion into a wound site and a wound drape for sealing enclosure of the foam pad at the wound site.

Reference is made to WO2014140578 that relates to the treatment of wound with negative pressure, but in particular it relates to wound closure. It makes use of a wound filing and is particularly useful for large wounds. However, it does not relate to the isolation of negative pressure and positive pressure (fluid) at the wound site.

Further, there are already some existing wound treating systems available in the art. This is ACTI V.A.C Negative Pressure Wound Therapy (NPWT) System which is a portable system designed for ambulatory patients. Designed to help patients resume their activities of daily living while still receiving the benefits of V.A.C.® Therapy.

There is PICO by Smith & Nephew, global product, which is a unique way of treating patients who would benefit from the application of NPWT. PICO is a revolutionary single use, canister free system, can save money compared to advance wound dressings by extending the interval between changes.

Further, there is also FDA cleared extriCARE® 2400 NPWT System which works to remove wound exudates, infectious material, and tissue debris from the wound bed and bring blood to the wound, which promotes faster healing. There is also Invia Liberty (of Medela, USA) which is a reusable NPWT system that can be used to treat a variety of wound types. It offers clinical flexibility with a range of pressure settings and therapy modes, while promoting patient mobility due to pump's compact size and lightweight design.

The Avance® Solo is a small and lightweight NPWT pump that maximizes patient freedom and mobility. Avance Solo allows for quick and easy discharge of patients from hospital while also reducing the challenges of logistics and administration for the caregiver. The VTG 3000, iVAC is portable system with a weight of about 600 gms. The system delivers continuous, variable and intermittent therapy with safety parameters for leakage, blockage, canister full, system tilt and inactive conditions.

The Smart NPWT (of Medical Development & Engineering, Pune) is a wound care modality used in modern healing process It is a treatment using sub-atmospheric pressure to increase blood flow remove bacteria and increase growth of granulation tissue in the wound.

WOUNDEX (of The Wedelia Surgical, Bangalore, India) is a CE certified NPWT Unit with unique features like impact pressure mode, GSM module, intermittent pressure mode, leakage caution system, light caution and nurse call system which can be used on various kind of wounds.

Most of the times, negative pressure wound therapy and fluid delivery therapies are used as separate treatment modes. Although there are prior arts available which disclose use of Negative pressure and oxygen together yet those systems are not efficient in lot of aspects. One of the limitations with existing prior arts is isolating negative pressure and positive pressure (fluid) at the wound site so that both the therapies can be provided at the wound site independently as well as simultaneously without interfering with each other. Yet another disadvantage with existing dual therapy dressings is difficulty in optimizing even distribution of negative pressure and oxygen at the wound site. Again, no such dual therapy dressing exists which can be used for treating a wide range of wounds that may include but not limited to infected wounds, exudating wounds, non-exudating wounds and the like. Another important factors to take care of is that existing dressings are made in various size and shape to accommodate various types of wounds which add to manufacturing and production cost. Further, most of the prior arts available for dual therapy dressing need several systematic procedural steps for application at wound site. This needs training for the clinician which is another problem from ease of use perspective.

Therefore, there is a dire need to provide an effective wound dressing to enhance wider range of bio mechanism favorable for would healing and which does not suffer the disadvantages associated with a conventional wound healing techniques and wound NPWT system.

SUMMARY OF THE INVENTION

The following disclosure presents a simplified summary of the invention in order to provide a basic understanding of some aspects of the invention. This summary is not an extensive overview of the present invention. It is not intended to identify the key/critical elements of the invention or to delineate the scope of the invention. Its sole purpose is to present some concept of the invention in a simplified form as a prelude to a more detailed description of the invention presented later.

An object of the present invention is to provide wound dressing for wound healing configured for equal distribution of negative pressure and fluid delivery at wound site to enhance wider range of biomechanism favourable for wound healing.

Another object of the present invention is to provide a wound dressing which promotes wound healing by a multi-therapeutic action which comprise of means of removing exudates, reducing inflammation, enhancing perfusion and controlling microbial growth.

Yet another object of the present invention is to provide a wound dressing with a unique arrangement of dressing components that can ensure one step procedure for wound site application and equal distribution of negative pressure and fluid delivery at the wound site covering the whole area.

Another object of the present invention is to provide a wound dressing with a provision for controlled delivery of negative pressure and fluid delivery independently as well as simultaneously to the wound site without interfering with each other.

Yet another object of the present invention is to provide a wound dressing that can be configured easily to accommodate wound of any size and shape.

Still another object of the present invention includes a simple design of the wound dressing that can easily be manufactured thus making it cost effective and affordable.

The wound care dressing is configured to provide therapeutic action by enhancing wider range of bio mechanism favorable for wound healing. The dressing comprises: at least one porous sheet; at least two flexible sheets having a first sheet and a second sheet attached to each other; a multi-channel conduit or a plurality of single channel conduits; at least one multi-channel tubes; side adhesive tapes and an optional wound contact layer. The principle, design and mechanism of this dressing can be adapted for any kind of wound at various anatomical sites of human body that may include but not limited to post-surgical wounds of amputated limbs, abdominal wounds, wounds at neck and other bony areas and the like.

Briefly, various aspects of the subject matter described herein are directed towards a wound healing and more particularly to wound healing dressing configured to enhance wider range of bio mechanism favourable for wound healing.

Other aspects, advantages, and salient features of the invention will become apparent to those skilled in the art from the following detailed description, which, taken in conjunction with the annexed drawings, discloses exemplary embodiments of the invention.

BRIEF DESCRIPTION OF THE ACCOMPANYING DRAWINGS

The above and other aspects, features, and advantages of certain exemplary embodiments of the present invention will be more apparent from the following description taken in conjunction with the accompanying drawings in which:

FIGS. 1 (*a*) and 1(*b*) show the various components of the basic wound dressing in accordance with an embodiment of the present invention.

FIG. 2(*a*) illustrates a porous sheet in accordance with one embodiment of the present invention.

FIG. 2(*b*) illustrates sectional profile of hollow channels/drills of the porous sheet in accordance with one embodiment of the present invention.

FIG. 2 (c) illustrates various possible arrangements of hollow channels within the porous sheet, in accordance with one embodiment of the present invention.

Figure 3A:
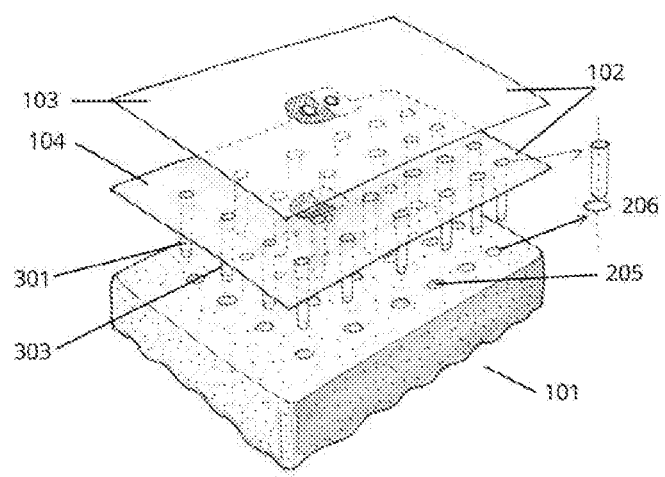
Figure 3B:
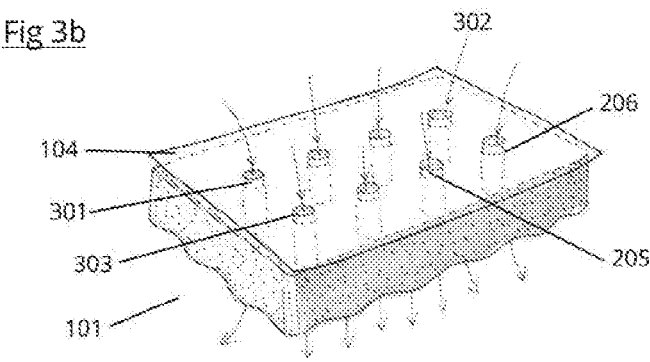

FIG. 3(a), FIG. 3(b) and FIG. 3(c) illustrate assembly of the various components of the basic wound dressing in accordance with an embodiment of the present invention.

Figure 3F:
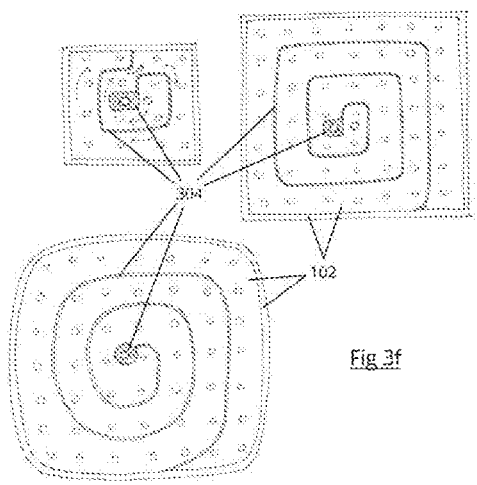

FIGS. 3(d), 3(e) and 3(f) illustrates an embodiment of opening channels of the dressing for negative pressure and fluid delivery.

Figure 4A:
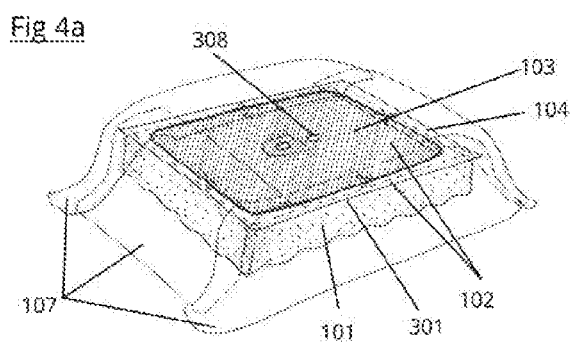
Figure 4B:
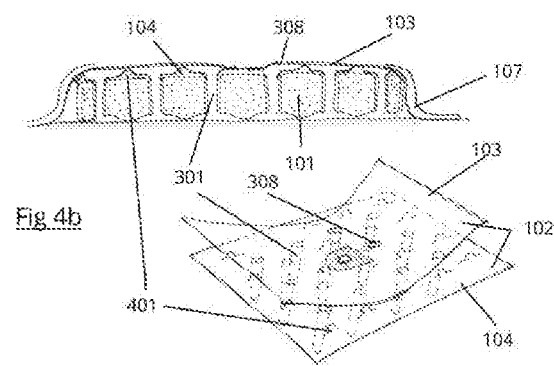

FIG. 4(a) and FIG. 4(b) illustrate the application of the dressing as well as isolation between negative pressure and fluid source within the dressing, in accordance with one embodiment of the invention.

Figure 5A:
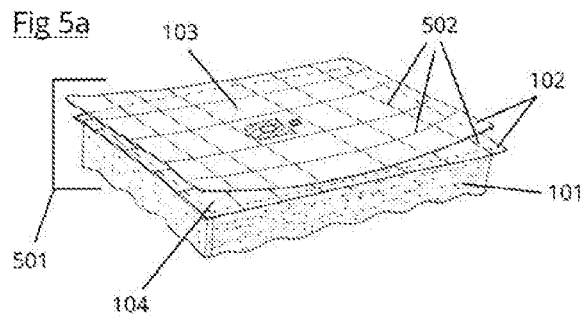
Figure 5B:
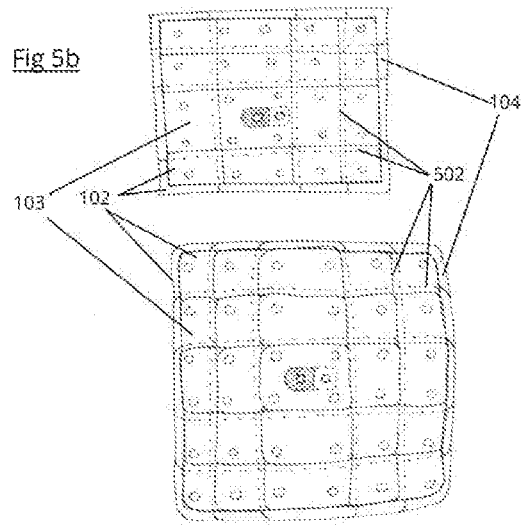
Figure 5C:
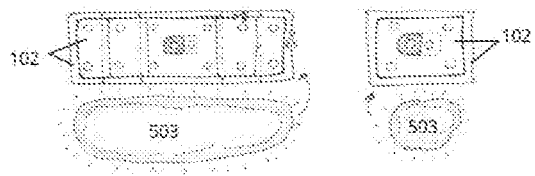
Figure 5C:
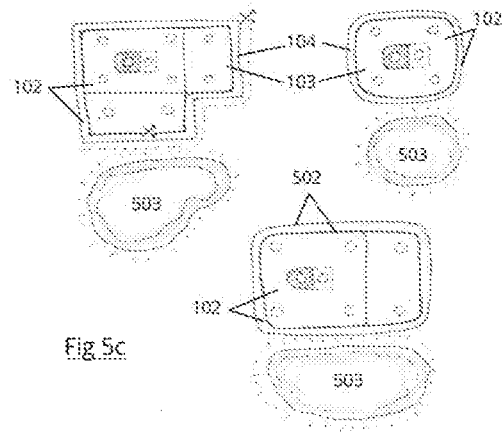
Figure 5D:
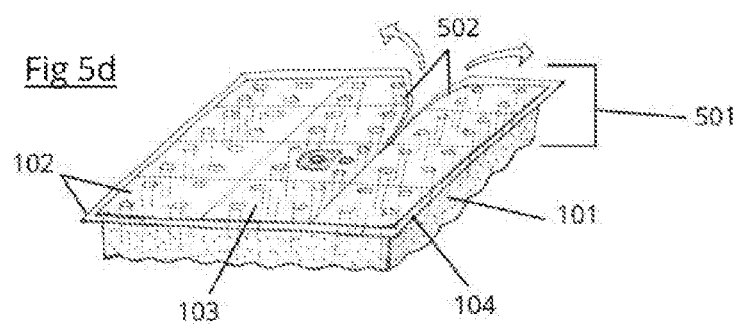

FIG. 5 (a), FIG. 5(b), FIG. 5(c) and FIG. 5(d) illustrate various embodiments to make the application of dressing a one-step procedure.

FIG. 6(a), FIG. 6(b), FIG. 6(c), FIG. 6 (d) illustrated various embodiments of the multichannel conduit and multichannel tubings.

Figure 7A:
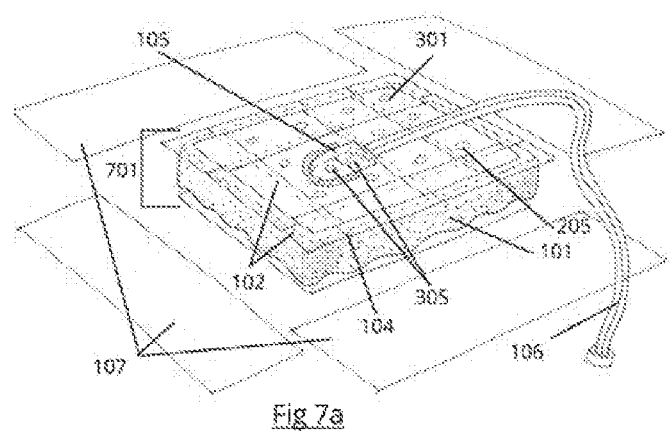
Figure 7B:
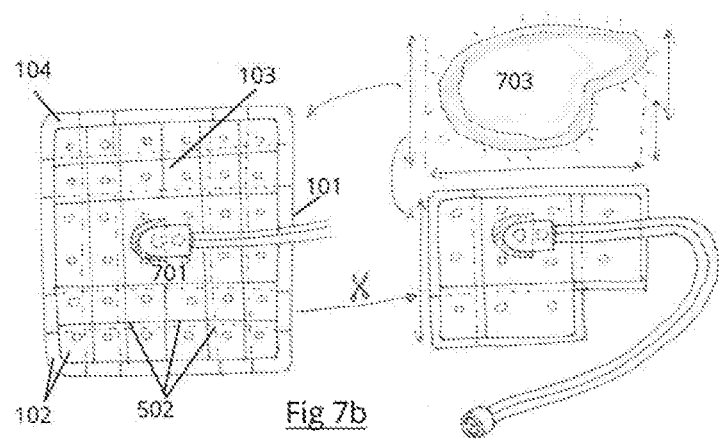
Figure 7C:
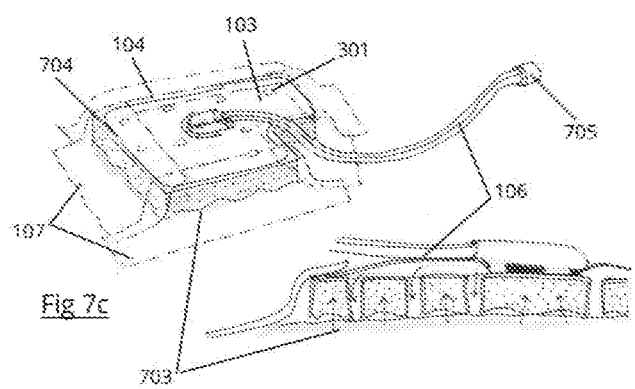

FIG. 7(a), FIG. 7(b), 7(c) illustrates the mechanism for applying the dressing to fit wound of any shape, in accordance with one embodiment of the present invention.

Figure 8:
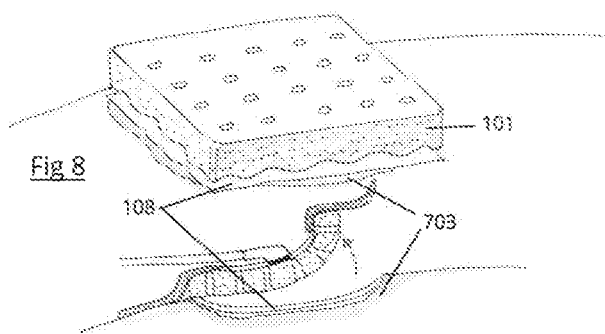

FIG. 8 illustrates application of wound contact layer at the wound site, in accordance with one embodiment of the present invention.

Figure 9:
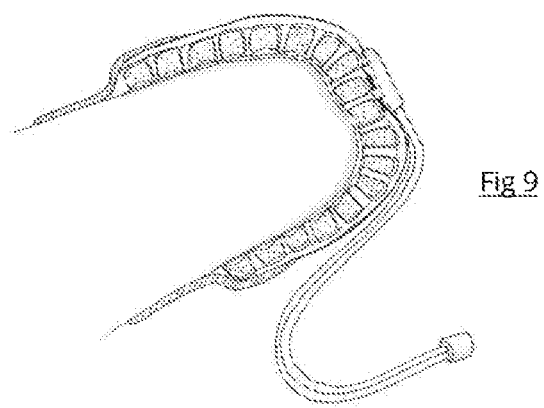
Figure 10:
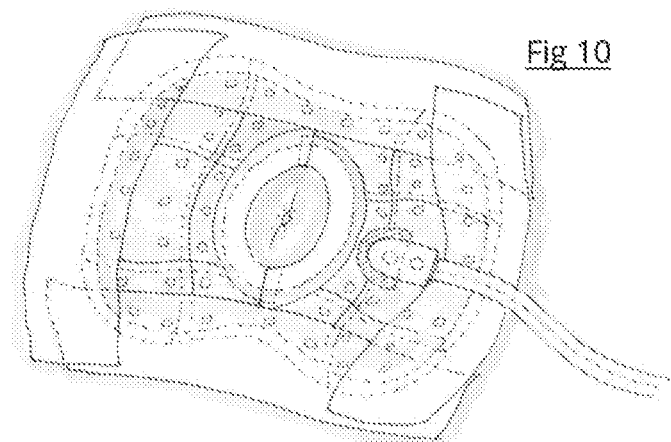

FIG. 9 illustrates an embodiment of the present invention for amputed wound site FIG. 10 illustrates an embodiment of the present invention for perinatal wounds Persons skilled in the art will appreciate that elements in the figures are illustrated for simplicity and clarity and may have not been drawn to scale. For example, the dimensions of some of the elements in the figure may be exaggerated relative to other elements to help to improve understanding of various exemplary embodiments of the present disclosure. Throughout the drawings, it should be noted that like reference numbers are used to depict the same or similar elements, features, and structures.

DETAILED DESCRIPTION OF THE PRESENT INVENTION

The following description with reference to the accompanying drawings is provided to assist in a comprehensive understanding of exemplary embodiments of the invention. It includes various specific details to assist in that understanding but these are to be regarded as merely exemplary.

Accordingly, those of ordinary skill in the art will recognize that various changes and modifications of the embodiments described herein can be made without departing from the scope of the invention. In addition, descriptions of well-known functions and constructions are omitted for clarity and conciseness.

In one embodiment, a multi-action wound dressing is provided for wound healing by a multi-therapeutic action. In the present invention fluid is defined as any matter that flows and which includes both gaseous and liquid state matters. This may include but not limited to water, saline water, oil, oxygen, air, liquid, medicine and the like.

The wound dressing will be adapted for multiple underlying mechanisms of wound healing process. In the system all the components may be integrated to provide various therapeutic actions that may include but not limited to, exudates removal, reducing inflammation, enhancing cell proliferation and controlling microbial growth. The various processes associated with the wound healing such as controlled delivery of negative pressure and fluid delivery may be occurring simultaneously or independently at the wound site without interfering each other. The arrangements of components in a manner can make it simple one step procedure for wound site application. The design arrangement of the wound dressing is in a manner to ensure equal distribution of negative pressure and fluid delivery at wound site across the whole area. The unique arrangement of components of wound dressing make the wound dressing system better designed and flexible enough to be used for wounds of different size and shapes.

In one embodiment, as shown in FIGS. 1(a) and 1(b), the basic overview of an embodiment of the dressing comprises: a porous sheet (101); two flexible sheets (102) having a first sheet (103) and a second sheet (104) attached to each other; multichannel conduits (105) or a plurality of single channel conduits; multichannel tubes (106), side adhesive tapes (107) and an optional wound contact layer (108)

In one embodiment, as shown in FIG. 2(a), wherein the porous sheet (101) may include a top planar surface (201), thickness (202) across which intermediate hollow channels/drills (205) are present so as to equally distribute negative pressure and fluid flow on the surface and a bottom uneven surface (203). The bottom uneven surface (203) lies on the surface of the wound and may have surface patterns (204). The pattern (204) may be wavy patterns and/or any other regular and/or irregular surface protrusion that allow intermediate gaps between wound surface and the bottom surface (203) of the porous sheet through which fluid can flow over the wound surface.

In one embodiment, the porous sheet (101) also include an intermediate hollow channels/drills (205) across the thickness (202) of the porous sheet (101) that creates an opening at the top planar surface (201) and the bottom uneven surface (203) of the porous sheet (101). The sectional profile (206) of hollow channels/drills (205) as shown in FIG. 2(b) can be of any geometrical shape that may include but not limited to circular, triangular or some random irregular shape.

Figure 2C:
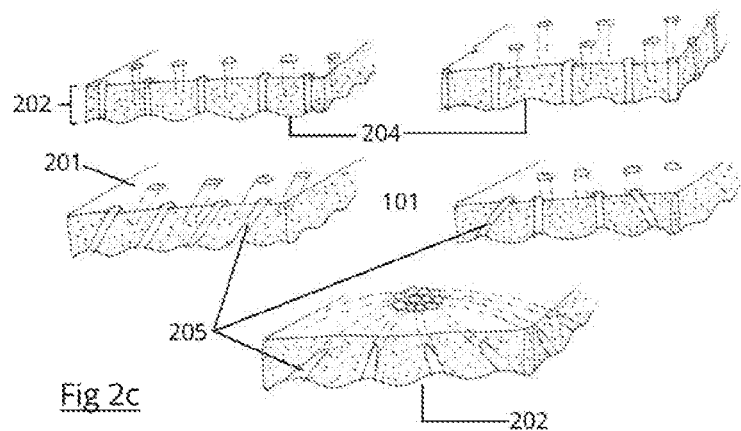

In one embodiment, there may be various physical and geometrical relationships between the positions and alignment of the hollow channels/drill (205) and the surface patterns (204) of the bottom uneven surface (203) of the porous sheet (101) as shown in FIG. 2c.

In one embodiment, the two flexible sheets (102) comprise of a first sheet (103) and a second sheet (104) as shown in FIG. 1a and FIG. 1b. The two flexible sheets (102) can be transparent as shown in FIG. 3a. In the embodiment the second sheet (104) may have a planar flexible surface having downward hollow protruded channels (301) that has sectional profiles (206) as that of hollow channels/drills (205) of the porous sheet (101). The protruded channels (301) are distributed on the second sheet (104) in such a way that those can fit the hollow channels/drills (205) of the porous sheet (101) as male-female connection as shown in FIG. 3b. In such a configuration the protruded channels (301) of the second sheet (104) carry fluid (302) to the wound site without interfering with the negative pressure wound therapy. The walls (303) of the protruded channels (301) act as barrier for liquid and gas.

In one embodiment, the first sheet (103) may include a planar flexible surface attached to the second sheet (104) at a merged area (304) in such a way that there is no gap between the two flexible sheets (102) in that particular area as shown in FIG. 3c. In another embodiment as shown in FIG. 3d there can be two or more of such areas where the first sheet (103) and second sheet (104) are attached in similar way. The process for attaching the two flexible sheets (102) in such fixed size merged area (304) can be use of adhesive, heat pressing, or any other means of Industrial bonding.

In one embodiment, the two flexible sheets (102) may further include openings (305) for providing negative pressure or fluid during therapies like negative pressure wound therapy and fluid therapy respectively. In one embodiment as shown in FIGS. 3(c), 3(d) and 3(e), a first opening (306) for negative pressure may be positioned on the merged area(s) (304) of the two flexible sheets (102) so that via the first opening negative pressure can be applied directly to the porous sheet (101) level. This first opening at the merged areas (304) create holes in both first sheet (103) and second sheet (104) simultaneously and isolates the negative pressure supply from rest of the space (307) between the first sheet (103) and second sheet (104). Another second opening (308) for fluid supply is (are) positioned on the first sheet (103) without creating hole in the second sheet (104). The fluids can be supplied via second opening (308) between the first sheet (103) and second sheet (104) without affecting the negative pressure wound therapy.

In an alternate embodiment, referring to FIG. 3 (f), the merged areas (304) between the two flexible sheets (102) can be configured in a particular way thereby allowing the flow of fluid radially outward from the central location. This kind of configuration allows the clinician to cut the dressing to any shape yet achieving uniform distribution of fluid across the dressing.

In one embodiment, during clinical setting as shown in FIG. 3(e), side adhesive tapes (107) may be used to seal the edges of the two flexible sheets (102) together with the underneath porous sheet (101) within the peripheral skin area of the wound site.

In an embodiment, as shown in FIG. 4(a), the area of the first sheet (103) may be kept slightly smaller than that of the second sheet (104) so that during sealing with the side adhesive tapes (107), the edges of first sheet (103) will get sealed with the second sheet (104) while sealing the two flexible sheets (102) with the skin surface. Due to this arrangement the supplied fluid through the second opening (308) remain within the two flexible sheets (102) and eventually flow through the protruded channels (301) of the second sheet (104). In a similar configuration as shown in FIG. 3e the supplied fluid will reach the wound site via the protruded channels (301).

In another embodiment, as shown in FIG. 4(b), either or both of the two flexible sheets (102) can further have an intermediate uneven surface patterns (401) to maintain a gap between the first sheet (103) and the second sheet (104), such that there is no hindrance to the fluid flow to all the areas within the two flexible sheets (102).

In one embodiment, in order to make this configuration easy, in a basic setup the two flexible sheets (102) and the porous sheet (101) may be provided in a merged setup (501) as shown in FIG. 5(a). The two flexible sheets (102) may include factory defined markings (502) on their surfaces as shown in FIG. 5a and FIG. 5b to guide the clinical practitioner to cut the two flexible sheets (102) along with the underneath porous sheet (101) at equal size as the wound area and at a right configuration. Further, as shown in FIG. 5c the same dressing can be cut down to apply on wound (503) of any size and shape. The markings (502) on the second sheet (104) may allow the clinical practitioner to cut the porous sheet (101) along with the second sheet (104). While the markings (502) on the first sheet (103) guide the clinical practitioner to cut the first sheet (103) in a smaller area than the second sheet (104), thus ensuring an airtight sealing between the first sheet (103) and second sheet (104) while sealing the two flexible sheets (102) together with the skin surface. In an alternative embodiment, as shown in FIG. 5d, the two flexible sheets (102) may composed of materials that can be easily teared along with the foam, by the hands of the clinician.

Figure 6A:
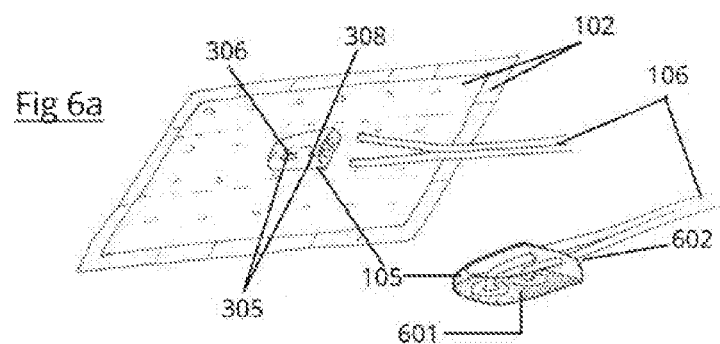
Figure 6B:
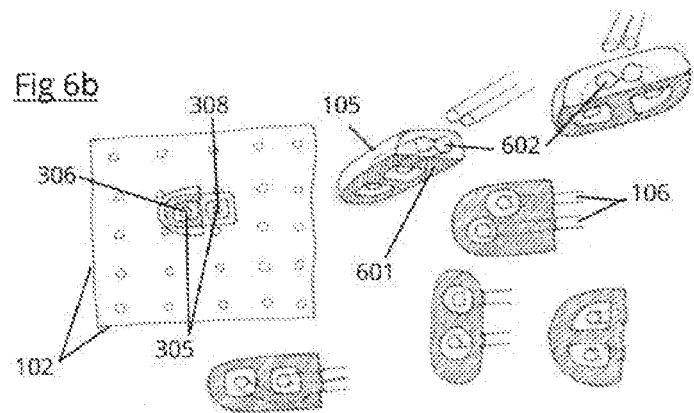
Figure 6C:
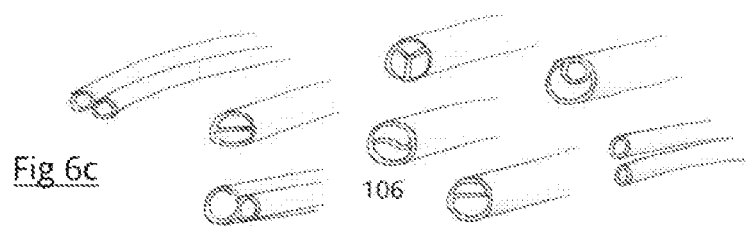

In one embodiment, as shown in FIG. 6(a), the openings (305) which include first opening (306) and second opening (308) may be covered with a multichannel conduit (105) that can allow attachment of multichannel tubes (106) to the dressing from the source of negative pressure and source of fluid. As shown in FIG. 6(b), the multichannel conduits (105) may be structurally designed to keep isolation between the source of negative pressure and source of fluid at an interface one (601) between multichannel conduits (105) and two flexible sheets (102) as well as at an interface (602) between multichannel conduit (105) and multichannel tubes (106). Variations of multichannel conduits (105) and multichannel tubes (106) are further shown in FIGS. 6 (b) and 6(c) respectively.

Figure 6D:
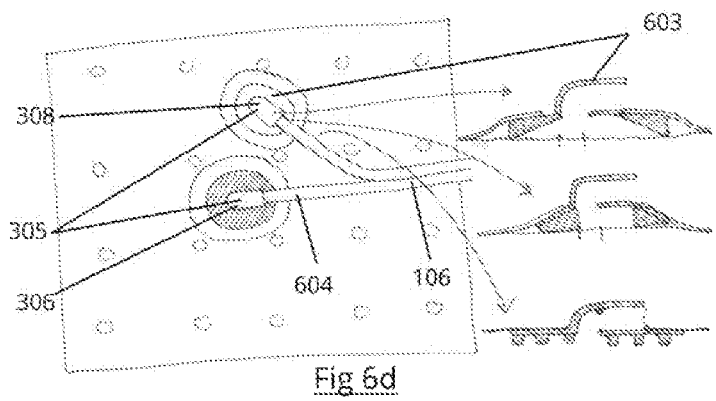

In an alternate embodiment, referring to FIG. 6(d), the openings (305) that includes first opening (306) and second opening (308) may be covered with a separate single channel conduits (603), which allows attachment of individual channels (604) of the multichannel tubes (106) to the dressing from the source of negative pressure and fluid. This provides a simpler approach without the need of designing a sophisticated multichannel conduit (105) as shown in FIG. 6(a).

In one embodiment, in a factory setting in which the dressing comes in a configuration where most of the components of the dressing except the side adhesive tapes (107) may come in a merged configuration (701) as shown in FIG. 7(a). The multichannel tubes (106) may be attached to the conduits (105), whereas the conduit (105) may be fixed to the openings (305) of the two flexible sheets (102). The porous sheet (101) underneath may be merged with the two flexible sheets (102) in such a way that the protruded channels (301) are distributed on the second sheet (104) so as to fit the hollow channels/drills (205) of the porous sheet (101) as a male-female connection.

In one embodiment, a standard wound care clinical case scenario is shown FIG. 7(b), the clinician may first check the size and shape of the wound. Then the wound dressing in the merged configuration as shown in FIG. 7 (a) may be cut down to match the wound site (703). The markings (502) on the second sheet (104) guide the clinician to match the porous sheet (101), along with the two flexible sheets (102) to the size and shape of the wound (703). The markings (502) on the first sheet (103) guide the clinician to cut the first sheet (103) slightly smaller in area than the second sheet (104). Further, as shown in FIG. 7(c) the clinician places the resultant custom sized dressing on the wound site (703) and uses the adhesive tapes (107) to seal all the edges of the dressing to the peripheral skin area surrounding the wound site (703) to create a vacuum seal for the negative pressure wound therapy. Simultaneously, sealing occurs between the edges (704) of the first sheet (103) and the second sheet (104) during this process further ensuring the flow of fluid only through the protruded channels (301) of the second sheet (104) to the wound site (703) without any other possible escape routes. The clinician then connects the other end (705) of the multichannel tubes (106) to the negative pressure and the fluid source.

In one embodiment, referring to FIG. 8, an optional liquid and gas permeable wound contact layer (108) can be used underneath the porous sheet (101), on top of the wound site (703), to prevent pain during dressing removal at the end of negative pressure wound therapy. The wound contact layer (108) may include special hydro phobic or waxy material coating such as paraffin, to prevent firm adherence of the porous sheet (101) to the wound site due to prolonged negative pressure wound therapy. In an alternative embodiment, similar results can be achieved by using such special hydrophobic or waxy material such as paraffin, to coat the outer surfaces of the porous sheet (101) without the need of using the wound contact layer (108)

The principle, design and the mechanism of the wound dressing system can be adapted for any kind of wounds at various anatomical site of human body that may include but not limited to post-surgical wounds of amputated limbs, abdominal wounds, wounds at neck and other bony areas. FIGS. 9 and 10 which illustrates two embodiments of dressing for such kind of wounds.

Some of the noteworthy features of the present invention are mentioned below:
1. The invention comprises a wound dressing that can be used for any kind of wound that may include but not limited to infected wound, exudating wound, non-exudating wound and the like. The dressing can be used for therapeutic combination of negative pressure and fluid delivery that makes the solution usable for treatment of more than one type of wound by taking care of various underlying mechanisms which contribute to wound healing process. The multi therapeutic action can comprise of means of removing exudate, reducing inflammation, enhancing perfusion and controlling microbial growth.
2. It is a simple yet unique approach to isolate negative pressure and positive pressure (fluid) at the wound site, so that negative pressure and positive pressure (fluid) can be provided at the wound site independently as well as simultaneously without interfering each other. This can be done by introducing the concept of having a merged area and unmerged area between the two flexible sheets as well as concept of hollow protrusions in the second sheet that fits the porous sheet above the wound site which are liquid and gas impermeable.
3. The dressing is engineered at the structural level to optimize even distribution of Negative pressure and fluid. This is done by following means:
   a) Channels for both the therapies evenly distributed over the dressing sheets.
   b) Structural modification to conventional porous sheet to get even distribution of both the therapies.
   c) Structural entities between the two sheets allow uniform distribution of fluid within the two flexible sheets to ensure further even distribution of fluid at the wound site through fluid carrying channels.
4. The present invention provides a single dressing that can be configured to accommodate wound of any size and shape. This can be achieved by uniform distribution of channels for both the therapies over the dressing, centrally placed conduit, markings on the surface of the dressing make the dressing applicable to wound of any size and shape.
5. The present invention reduces complexities of delivering the two therapies by using a simplified design. Structural design and arrangement of various components of the dressing make it compact enough which can be packed and distributed as factory configuration along with side tapes. So whole process of dressing application can be reduced to one step procedure. The simple design of the dressing can be easily manufactured with conventional techniques thus saving cost to make it affordable.

Some of the non-limiting advantages of the present invention over the prior art are mentioned below:
1. The existing NPWT dressings are not used for long duration on infected wounds. The wound dressing system of the present invention use fluid delivery which provides antimicrobial property to the dressing and can be used for longer duration even for infected wounds.
2. In current practice, the dressing for NPWT therapy is a multi-step time consuming process. The dressing of the present invention is comparatively a simpler which requires less number of application steps thereby making it easy to use and saving time effort of the health care provider.
3. The wound dressing of the present invention is better designed than existing dressings and allows for equal distribution of pressure and fluid thus resulting in uniform healing of the wound in lesser time.
4. The dressing of the present invention can be used for various kinds of wounds.
5. The simple design and flexibility of the dressing can be easily manufactured with conventional techniques thus saving cost to make it affordable and is usable for wounds of any shape and size.
6. A single dressing that can be configured easily to accommodate wound of any shape and size, which is achieved by uniform distribution of channels for both the therapies over the dressing, centrally placed conduits, markings on the surface that can accommodate wound of any shape and size.
7. The dressing can be arranged in a compact form which can be packed and distributed as factory configuration along with side tapes.
8. The whole process of dressing application can be reduced to a one step procedure Although a wound dressing for negative pressure wound treatment have been described in language specific to structural features and/or methods, it is to be understood that the embodiments disclosed in the above section are not necessarily limited to the specific features or methods or devices described herein. Rather, the specific features are disclosed as examples of implementations of the wound dressing.

The invention claimed is:
1. A wound dressing device for a combined negative pressure and fluid delivery healing technique, the wound dressing comprising:
a porous sheet (101) having a top planar surface (201), a thickness (202) across which intermediate hollow channels/drills (205) are present so as to equally distribute negative pressure and fluid flow on the top planar surface, and a bottom uneven surface (203) having a surface pattern (204) meant to lie on the surface of a wound, wherein the pattern (204) of the bottom uneven surface (203) is a wavy pattern and/or any other regular and/or irregular surface protrusion configured to create intermediate gaps between the wound surface and the bottom surface (203) of the porous sheet through which fluid can flow over the wound surface;
flexible sheets (102) having a planar flexible surface comprising a first sheet (103) and a second sheet (104) attached to each other at merge areas (304), the said second sheet (104) having downward hollow protruded channels (301), said flexible sheets (102) having mul- tiple openings (305) for providing negative pressure or fluid during negative pressure wound therapy and fluid therapy;

such that said downward hollow protruded channels (301) of the second sheet (104) having sectional profiles (206) as that of the hollow channels/drills (205) of the porous sheet (101) such that a male-female connection is established between the said protruded channels (301) and the said hollow channels/drills (205);

said openings (305) covered with a conduit (105) allowing the attachment of multichannel tubes (106) to the wound dressing from the source of negative pressure and source of fluid; and a side adhesive tapes (107) meant for sealing the edges of the two flexible sheets (102) together with the underneath porous sheet (101) within the peripheral skin area of wound (703), wherein the multiple openings (305) comprises a first opening (306) for negative pressure supply adapted to create holes in the one of said merge areas (304) of said first sheet (103) and said second sheet (104) simultaneously isolating the negative pressure supply from the rest of the space (307) between the first sheet (103) and second sheet (104); and a second opening (308) for fluid supply positioned on the first sheet (103) without creating a hole in the second sheet (104) thereby supplying fluids via second opening (308) between the first sheet (103) and second sheet (104) without affecting the negative pressure wound therapy; such that said fluid spreads over said second sheet and flows through the male-female connection established between the said protruded channels (301) and the said hollow channels/drills (205) to the wound site.

2. The wound dressing device as claimed in claim 1, wherein said conduit (105) comprises multichannel conduits allowing the attachment of said multichannel tube (106), or said conduit (105) comprises separate single channel (603) conduits allowing the attachment of individual channels (604) of multichannel tubes (106).

3. The wound dressing device as claimed in claim 1, further comprising a wound contact layer (108) having a hydrophobic or waxy material coating underneath the porous sheet (101), or the outer surfaces of the porous sheet (101) are coated with a hydrophobic or waxy material.

4. The wound dressing device as claimed in claim 1, wherein the positions and alignment of the hollow channels/drill (205) and the surface patterns (204) of the bottom uneven surface (203) of the porous sheet (101) are physically and geometrically related.

5. The wound dressing device as claimed in claim 1, wherein the flexible sheets (102) are transparent.

6. The wound dressing device as claimed in claim 1, wherein the protruded channels (301) of the second sheet (104), defined by walls (303), are configured to carry fluid (302) to the wound (703) without interfering with the negative pressure wound therapy.

7. The wound dressing device as claimed in claim 1, wherein the attachment of the first sheet (103) with the second sheer (104) at merge areas (304) is such that there is no gap between the two flexible sheets (102) in the merge area (304).

8. The wound dressing device as claimed in claim 1, wherein the attachment of the first sheet (103) with the second sheet (104) is by means of adhesive, heat pressing, or another means of industrial bonding.

9. The wound dressing device as claimed in claim 1, wherein the merged areas (304) between the two flexible sheets (102) are configured to allow the flow of fluid radially outward from a central location.

10. The wound dressing device as claimed in claim 1, wherein either or both of the two flexible sheets (102) comprise an intermediate uneven surface pattern (401) to maintain a gap between the first sheet (103) and the second sheet (104), such that there is no hindrance to the fluid flow to all the areas within the two flexible sheets (102).

11. The wound dressing device as claimed in claim 1, wherein the conduits (105) are structurally designed to keep isolation between the source of negative pressure and source of fluid at an interface (601) between conduits (105) and two flexible sheets (102) and at another interface (602) between conduit (105) and multichannel tubes (106).

12. The wound dressing device as claimed in claim 1, wherein the components of the dressing except the side adhesive tapes (107) is in a merged configuration (701) wherein the setup of the two flexible sheets (102) and the porous sheet (101) is provided in a merged setup (501) with factory defined markings (502) on their surface;

the multichannel tubes (106) are attached to the conduits (105), whereas the conduit (105) is fixed to the openings (305) of the two flexible sheets (102).

13. A method of dressing a wound comprising applying the wound dressing device as claimed in claim 12, the method further comprising:

cutting down the wound dressing device based on the measured size and shape of the wound by a user wherein markings (502) on the second sheet (104) guide a user to match the porous sheet (101) and the two flexible sheets (102) to the size and shape of the wound (703), and markings (502) on the first sheet (103) guide the user to cut the first sheet (103) slightly smaller in area than the second sheet (104).

14. A method of dressing a wound as claimed in claim 13, the method further comprising: placing the resultant custom sized cut dressings on the wound (703); sealing all the edges of the dressing to the peripheral skin area surrounding the wound (703) by means of adhesive tapes (107) creating a vacuum seal for negative pressure wound therapy; and simultaneously sealing the edges (704) of the first sheet (103) and the second sheet (104) further ensuring the flow of fluid only through the protruded channels (301) of the second sheet (104) to the wound (703) without any other escape routes, by the user.

15. A method of dressing a wound as claimed in claim 14, the method further comprising: connecting an end (705) of the multichannel tubes (106) to the negative pressure and the fluid source by the user.

16. A method of dressing a wound comprising applying the wound dressing device as claimed in claim 1, the method further comprising:

placing by the user, the optional liquid and gas permeable wound contact layer (108) underneath the porous sheet (101), on top of the wound (703).

17. The wound dressing device of claim 1, wherein the first sheet (103) and second sheet (104) are attached to each other at merge areas (304); and the multiple openings (305) comprises:

a first opening (306) for negative pressure positioned on one of the merged areas (304) of the flexible sheets (102) such that by means of said first opening negative pressure can be applied directly to the porous sheet (101); and a second opening (308) for fluid supply positioned on the first sheet (103) without creating a hole in the second sheet (104) for supply of fluids without affecting the negative pressure wound therapy.

\* \* \* \* \*